US009486323B1

(12) United States Patent
Hibri et al.

(10) Patent No.: US 9,486,323 B1
(45) Date of Patent: Nov. 8, 2016

(54) NUCLEAR IMPLANT APPARATUS AND METHOD FOLLOWING PARTIAL NUCLECTOMY

(71) Applicant: SPINAL STABILIZATION TECHNOLOGIES LLC, San Antonio, TX (US)

(72) Inventors: Nadi S. Hibri, San Antonio, TX (US); W. Loren Francis, San Antonio, TX (US); Mark A. Novotny, San Antonio, TX (US)

(73) Assignee: Spinal Stabilization Technologies LLC, San Antonio, TX (US)

( * ) Notice: Subject to any disclaimer, the term of this patent is extended or adjusted under 35 U.S.C. 154(b) by 0 days.

(21) Appl. No.: 14/934,987

(22) Filed: Nov. 6, 2015

(51) Int. Cl.
    *A61F 2/44*      (2006.01)

(52) U.S. Cl.
    CPC .............. *A61F 2/441* (2013.01); *A61F 2/442* (2013.01); *A61F 2002/444* (2013.01)

(58) Field of Classification Search
    CPC ....................... A61F 2/442; A61F 2002/444
    See application file for complete search history.

(56) References Cited

U.S. PATENT DOCUMENTS

| | | | |
|---|---|---|---|
| 4,187,390 A | 2/1980 | Gore | 174/102 R |
| 4,478,898 A | 10/1984 | Kato | 428/36.91 |
| 4,619,641 A | 10/1986 | Schanzer | 604/8 |
| 4,743,480 A | 5/1988 | Campbell et al. | 428/36.5 |
| 5,152,782 A | 10/1992 | Kowligi et al. | 623/1.46 |
| 5,192,310 A | 3/1993 | Herweck et al. | 623/1.27 |
| 5,466,509 A | 11/1995 | Kowligi et al. | 428/141 |
| 5,628,786 A | 5/1997 | Banas et al. | 623/1.13 |
| 5,827,327 A | 10/1998 | McHaney et al. | 623/1.44 |
| 5,860,425 A | 1/1999 | Benderev et al. | 128/898 |
| 5,865,845 A | 2/1999 | Thalgott | 623/17.16 |
| 5,879,366 A | 3/1999 | Shaw et al. | 606/213 |
| 5,888,226 A | 3/1999 | Rogozinski | 623/17.16 |
| 5,910,277 A | 6/1999 | Ishino et al. | 264/127 |
| 5,928,284 A | 7/1999 | Mehdizadeh | 623/17.13 |
| 5,935,147 A | 8/1999 | Kensey et al. | 606/213 |
| 5,954,767 A | 9/1999 | Pajotin et al. | 623/23.72 |
| 5,972,022 A | 10/1999 | Huxel | 606/215 |
| 5,976,174 A | 11/1999 | Ruiz | 606/213 |
| 6,001,125 A | 12/1999 | Golds et al. | 623/23.7 |
| 6,001,130 A | 12/1999 | Bryan et al. | 623/17.16 |
| 6,007,570 A | 12/1999 | Sharkey et al. | 607/96 |
| 6,007,575 A | 12/1999 | Samuels | 623/1.15 |
| 6,019,793 A | 2/2000 | Perren et al. | 623/17.16 |
| 6,036,724 A | 3/2000 | Lentz et al. | 623/1.1 |
| 6,126,682 A | 10/2000 | Sharkey et al. | 607/96 |
| 6,140,452 A | 10/2000 | Felt et al. | 528/60 |

(Continued)

*Primary Examiner* — Ellen C Hammond
(74) *Attorney, Agent, or Firm* — Norton Rose Fulbright US LLP

(57) ABSTRACT

An expandable implant for augmenting a damaged or otherwise torn posterior annulus fibrosus. The implant is deployable into an evacuated posterior disc space following a subtotal nuclectomy. The implant includes an inflatable balloon which is fixed to the annulus fibrosus to protect against migration. When inflated with a curable polymer, the posterior wall of the implant is intimately disposed along the inner surface of the annulus fibrosus to provide a substantially fluid-tight seal of the annular tear or defect and reinforce the weakened posterior annulus. The anterior wall of the implant sequesters the nuclear remnant to guard against disc remnant herniation. The implant can restore intradiscal pressure and disc height. An integrated posterior reinforcement band creates a strong, yet flexible and resilient structure, resistant to penetration of the implant through the annular tear or defect.

18 Claims, 17 Drawing Sheets

(56) References Cited

U.S. PATENT DOCUMENTS

| | | | |
|---|---|---|---|
| 6,180,848 B1 | 1/2001 | Flament et al. | 623/11.11 |
| 6,206,921 B1* | 3/2001 | Guagliano | A61F 2/441 |
| | | | 606/92 |
| 6,224,630 B1 | 5/2001 | Bao et al. | 623/17.16 |
| 6,344,054 B1 | 2/2002 | Parodi | 623/1.13 |
| 6,361,637 B2 | 3/2002 | Martin et al. | 156/187 |
| 6,398,803 B1 | 6/2002 | Layne et al. | 623/1.13 |
| 6,402,750 B1 | 6/2002 | Atkinson et al. | 606/279 |
| 6,419,704 B1 | 7/2002 | Ferree | 623/17.12 |
| 6,428,576 B1 | 8/2002 | Haldimann | 623/17.16 |
| 6,436,143 B1 | 8/2002 | Ross et al. | 623/17.16 |
| 6,673,103 B1 | 1/2004 | Golds et al. | 623/1.13 |
| 6,780,497 B1 | 8/2004 | Walter | 428/311.51 |
| 6,852,223 B2 | 2/2005 | Huang et al. | 210/500.36 |
| 6,893,466 B2 | 5/2005 | Trieu | 623/17.16 |
| 7,273,497 B2 | 9/2007 | Ferree | 623/17.16 |
| 7,297,158 B2 | 11/2007 | Jensen | 623/1.44 |
| 8,419,839 B2 | 4/2013 | Shimatani | 96/12 |
| 8,449,660 B2 | 5/2013 | Shimatani et al. | 96/11 |
| 8,979,931 B2 | 3/2015 | Stad et al. | 623/17.12 |
| 2002/0151979 A1* | 10/2002 | Lambrecht | A61B 17/70 |
| | | | 623/17.16 |
| 2002/0198588 A1 | 12/2002 | Armstrong et al. | 623/1.13 |
| 2003/0028251 A1 | 2/2003 | Mathews | 623/17.16 |
| 2003/0040772 A1 | 2/2003 | Hyodoh et al. | 606/200 |
| 2003/0114917 A1 | 6/2003 | Holloway et al. | 623/1.13 |
| 2003/0153976 A1* | 8/2003 | Cauthen, III | A61F 2/441 |
| | | | 623/17.16 |
| 2004/0220672 A1* | 11/2004 | Shadduck | A61F 2/30965 |
| | | | 623/17.16 |
| 2005/0015150 A1 | 1/2005 | Lee | 623/17.12 |
| 2005/0137675 A1 | 6/2005 | Dubson et al. | 623/1.4 |
| 2006/0253132 A1* | 11/2006 | Evans | A61F 2/442 |
| | | | 606/151 |
| 2007/0255285 A1* | 11/2007 | Trieu | A61B 17/7097 |
| | | | 606/86 R |
| 2008/0119943 A1 | 5/2008 | Armstrong et al. | 623/23.7 |
| 2009/0163994 A1 | 6/2009 | Quigley et al. | 623/1.15 |
| 2010/0191335 A1* | 7/2010 | Root | A61F 2/441 |
| | | | 623/17.16 |
| 2010/0193999 A1 | 8/2010 | Anneaux et al. | 264/438 |
| 2012/0316648 A1* | 12/2012 | Lambrecht | A61B 17/320708 |
| | | | 623/17.16 |

* cited by examiner

NUCLEAR IMPLANT APPARATUS AND METHOD FOLLOWING PARTIAL NUCLECTOMY

BACKGROUND

1. Field of the Disclosure

The present disclosure relates generally to spinal surgery and more particularly to a method and apparatus for reinforcing a torn or damaged annulus fibrosus.

2. Description of Related Art

Spinal discs typically have an intact annulus fibrosus throughout life that confers normal resistance to applied forces. Degenerating discs, however, exhibit mechanical failure of the disc. A common mechanical failure is radial tears in the annulus fibrosus.

Radial tears of the annulus fibrosus are characteristic of all degenerating intervertebral discs and are often associated with loss of disc height, segmental instability and pain. By definition, a radial tear is a defect that extends through all layers of the annulus fibrosus, from its interior margin to the periphery of the disc.

Radial tears are found most commonly in the lumbar spine and are most prevalent at the L4-L5 and L5-S1, disc levels. Most radial tears involve the posterior annulus and occur without disc herniation, even in patients with clinical findings typical of a herniated disc. In the lumbar region, pain is often referred to a lower extremity. The referred pain may be difficult to distinguish clinically from radiculopathy of a herniated nucleus pulposus compressing a spinal nerve.

Breakdown of the nucleus pulposus generates fluids and tissues that may leak outward through the radial tear, causing inflammation of adjacent meninges and innervated granulation tissue along the radial tear.

The disruption of the annulus fibers by a radial tear is associated with loss of intradiscal pressure and disc height resulting in hypermobility or instability of the motion segment at the level of the affected disc. It is postulated that the spinal instability permitted by a radial tear may cause pain by straining the facet joints and connective tissues that extend across the degenerating disc.

The associated increased mobility may produce intermittent nerve root compression at spinal levels containing a radial tear. Intermittent occult spinal stenosis, lateral recess stenosis and neural foraminal stenosis may occur during changes in posture and physiologic loading of the spine.

Functional tests such as discography may demonstrate radial tears at multiple levels and identification of the symptomatic radial tear may be difficult to identify. The value of discography for identifying the symptomatic disc level and for predicting the outcome from spinal fusion has been debated.

Physicians sometimes make iatrogenic holes or annulotomies in various sizes and shapes and locations into the annulus as part of surgical procedures to address contained disc herniation or symptomatic radial tears.

In recent years, there has been increasing interest in repair, regeneration and support of the torn annulus fibrosus to restore the normal function of the disc. There is also interest in repairing radial tears or postsurgical annular defects to prevent recurrence of disc herniations and to slow the degenerative process after nuclectomy, in the context of successful treatment of different types of painful spinal conditions.

Annular repair, whether biologic or surgical, is a developing technology to address symptomatic annular tears, with or without disc herniations, or in surgical treatments of spinal conditions.

A number of surgical techniques and implants are currently under development and additional clinical data are expected in the next several years. Absorbable gelatin sponge (i.e., gel foam) appears to have promise. However, clinical testing has only been done on small size defects, and it is difficult to extrapolate this model to a nuclectomy. Sutures with anchors (for example, Xclose and Inclose, Anulex Technologies, Inc., Minnetonka, Minn.) have been introduced commercially and are currently undergoing a U.S. Food and Drug Administration (FDA) trial. Barricaid (Intrinsic Therapeutics, Inc., Woburn, Mass.) is a commercially available implant that anchors into the vertebral body and supports a woven mesh barrier inserted into the defect.

In an effort to reduce tissue damage associated with surgical intervention, there is a need to utilize minimally invasive surgical access or percutaneous access. In younger patients with an annular tear or disc herniation who have an otherwise undamaged or minimally degenerated annulus fibrosus and nucleus pulposus, a partial or targeted nuclectomy may be preferable to a total nuclectomy.

Current surgical procedure approaches, access and tools limit the surgeon's ability to determine the position, size and shape of the cleared disc space. This lack of precision presents difficulty in designing, sizing, placement and securement of a nuclear implant. Improper nuclear implant placement may interfere with biomechanical behavior of the spinal segment. This also increases the likelihood of migration and expulsion of the implant.

In sum, an annular tear or defect is clinically significant and requires treatment. However, commercially available treatments for an annular tear or other damage to an annulus fibrosus have many problems and/or disadvantages. Various embodiments of the present disclosure may mitigate or solve one or more of the problems and/or disadvantages.

SUMMARY

According to an exemplary aspect of the present disclosure, an apparatus for reinforcing a damaged annulus fibrosus comprises an inflatable balloon having a first end and a second end, wherein a posterior portion of the inflatable balloon is adapted to seal against an annulus fibrosus; a first anchor coupled to the first end of the inflatable balloon, the first anchor being adapted to anchor the first end of the inflatable balloon to a first location of the annulus fibrosus at a first lateral side of the annulus fibrosus; and a second anchor coupled to the second end of the inflatable balloon, the second anchor being adapted to anchor the second end of the inflatable balloon to a second lateral side of the annulus fibrosus.

The posterior portion of the inflatable implant may comprise a reinforcing layer coupled to a posterior side of the balloon so that the posterior portion is substantially non-compliant, and an anterior portion of the balloon may comprise a silicone material so that the anterior portion is substantially compliant.

The inflatable balloon may comprise any elastomeric biocompatible material suitable for long-term human implantation, such as silicone or PTFE. The inflatable balloon may comprise an electrospun polymeric material. The inflatable balloon may further comprise a carbon layer disposed on an inner surface of the inflatable balloon. The PTFE material may be porous.

The first anchor may comprise at least one inflation port for injecting an inflation material into the inflatable balloon.

The second anchor may further comprise at least one inflation port for injecting an inflation material into the inflatable balloon.

A curable material may be disposed in the inflatable balloon. A gas may be disposed in the inflatable balloon.

The inflatable balloon may comprise an anterior portion with different properties than the posterior portion. The posterior portion may be less compliant than the anterior portion. The posterior portion may comprise multiple layers.

The inflatable balloon may comprise multiple layers. The multiple layers may be adapted to provide different properties to the inflatable balloon.

An outer layer of the posterior portion may comprises an opening for allowing an inner layer of the posterior portion to protrude therethrough upon inflation.

The first anchor may comprise an expanded portion for preventing the first anchor from being pulled through the annulus fibrosus thereby mitigating against migration or expulsion.

The second anchor may comprise a retaining member with an expanded portion for helping to prevent the second anchor from being pulled through the annulus fibrosus. The retaining member may comprise a retaining ring with at least one opening for slidably receiving a slidable plate with at least one aperture for retaining a string extending from the second anchor.

The inflatable balloon may comprises multiple layers. The multiple layers may be adapted to provide different properties to the inflatable balloon.

The inflatable balloon may comprise a first chamber and a second chamber disposed entirely within the first chamber.

The second anchor may comprise first and second loops of material extending from the second anchor. A retaining member for engaging one of the first and second loops of material may be provided.

According to another exemplary aspect, the present disclosure is directed to a method of reinforcing the posterior of an annulus fibrosus, comprising inserting first and second cannulas through first and second annulotomies located on first and second sides of the posterior of an annulus fibrosus to gain access to a nuclear disc space; performing a subtotal nuclectomy to create a cavity extending between the first and second cannula, wherein a posterior side of the cavity is formed by the annulus fibrosus and the anterior side of the cavity is formed by a nuclear remnant; inserting an inflatable implant into the cavity formed by the subtotal nuclectomy so that a first end of the implant is located at the first annulotomy and a second end of the implant is located at the second annulotomy; inflating the implant with a curable medium so that implant substantially fills the cavity and presses against the annulus fibrosus to form a substantially fluid tight seal with the annulus fibrosus; anchoring the first end of the implant to the first annulotomy; and anchoring the second end of the implant to the second annulotomy.

The posterior portion of the annulus fibrosus may have a defect, and the first and second annulotomies may be spaced away from the defect on first and second sides of the defect.

The first and second annulotomies may be located on the posterolateral sides of the annulus fibrosus.

The steps of anchoring the first and second ends of the implant to the first and second annulotomies may comprise removing the first and second cannulas so that the first and second annulotomies engage the first and second ends of the implant.

The step of inserting the inflatable implant into the cavity may comprise deploying the implant into the cavity through the first cannula and may further comprise snaring the end of the implant through the second cannula and maneuvering the balloon into position.

The step of anchoring the second end of the implant may comprise attaching a retaining member to the second end of the implant, wherein the retaining member is larger than the second annulotomy.

The step of expanding the implant may further comprise inflating an interior chamber with a gaseous medium.

According to another exemplary aspect, the present disclosure is directed to a method of reinforcing a posterior annulus fibrosus comprises accessing a nuclear space formed by the annulus fibrosus; performing a partial nuclectomy to create a cavity extending from a first lateral side of the annulus to a second lateral side of the annulus, wherein a posterior side of the cavity is formed by an inner wall of the annulus fibrosus and an anterior side of the cavity is formed by a nucleus remnant; inserting an inflatable balloon with a first end and a second end into the cavity formed by the partial nuclectomy; inflating the inflatable balloon with a curable medium; anchoring the first end of the inflatable balloon to the annulus fibrosus on the first lateral side of the annulus fibrosus; and anchoring the second end of the inflatable balloon to the annulus fibrosus on the second lateral side of the annulus fibrosus.

The step of accessing the nuclear space may comprise obtaining bilateral posterolateral percutaneous access with first and second cannulas at the first and second sides of the annulus fibrosus.

The inflatable balloon may extends from the first cannula to the second cannula.

The method may further comprise withdrawing the first and second cannulas, so that first and second annulotomies engage the first and second ends of the balloon to anchor the first and second ends of the balloon to the annulus fibrosus.

The inflatable balloon may be deployed through the first cannula into the cavity. The balloon may be snared through the second cannula and maneuvered into position.

A portion of the inflatable balloon which is adapted to protrude from the inflatable balloon may be aligned with an annular defect, and the inflatable balloon may be inflated so that the balloon protrudes into the annular defect. The annular defect may comprise a defect caused by one of a herniated nucleus pulposus or an iatrogenic defect.

The balloon may form a substantially fluid tight seal with the annulus fibrosus.

The balloon may substantially prevent leakage of fluids out of the posterior of the annulus fibrosus.

In another aspect of the present disclosure, an anchor for anchoring a nuclear implant to an annulus fibrosus through an annulotomy may comprise an anchor member sized to fit through the annulotomy; at least one loop of material extending from the anchor member; and a retaining member with an aperture for receiving and engaging the at least one loop of material, the retaining member being larger than the annulotomy.

The retaining member may comprise a retaining ring and at least one movable member which is movable between an open position and a closed position, wherein the movable member has an opening for receiving the at least one loop of material so that loop of material is movable when the plate is in an open position and immovable when the plate is in a closed position.

The at least one loop of material may comprise an anchor loop. The at least one loop of material may further comprise a second loop of material for allowing a user to snare the second loop of material.

The term "coupled" is defined as connected, although not necessarily directly. The terms "a" and "an" are defined as one or more unless this disclosure explicitly requires otherwise. The terms "substantially," "approximately," and "about" are defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, or a component of a system, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

A device, system, or component of either that is configured in a certain way is configured in at least that way, but it can also be configured in other ways than those specifically described.

Any embodiment of any of the systems and methods can consist of or consist essentially of—rather than comprise/include/contain/have—any of the described elements, features, and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are presented below.

DETAILED DESCRIPTION

Figure 1:
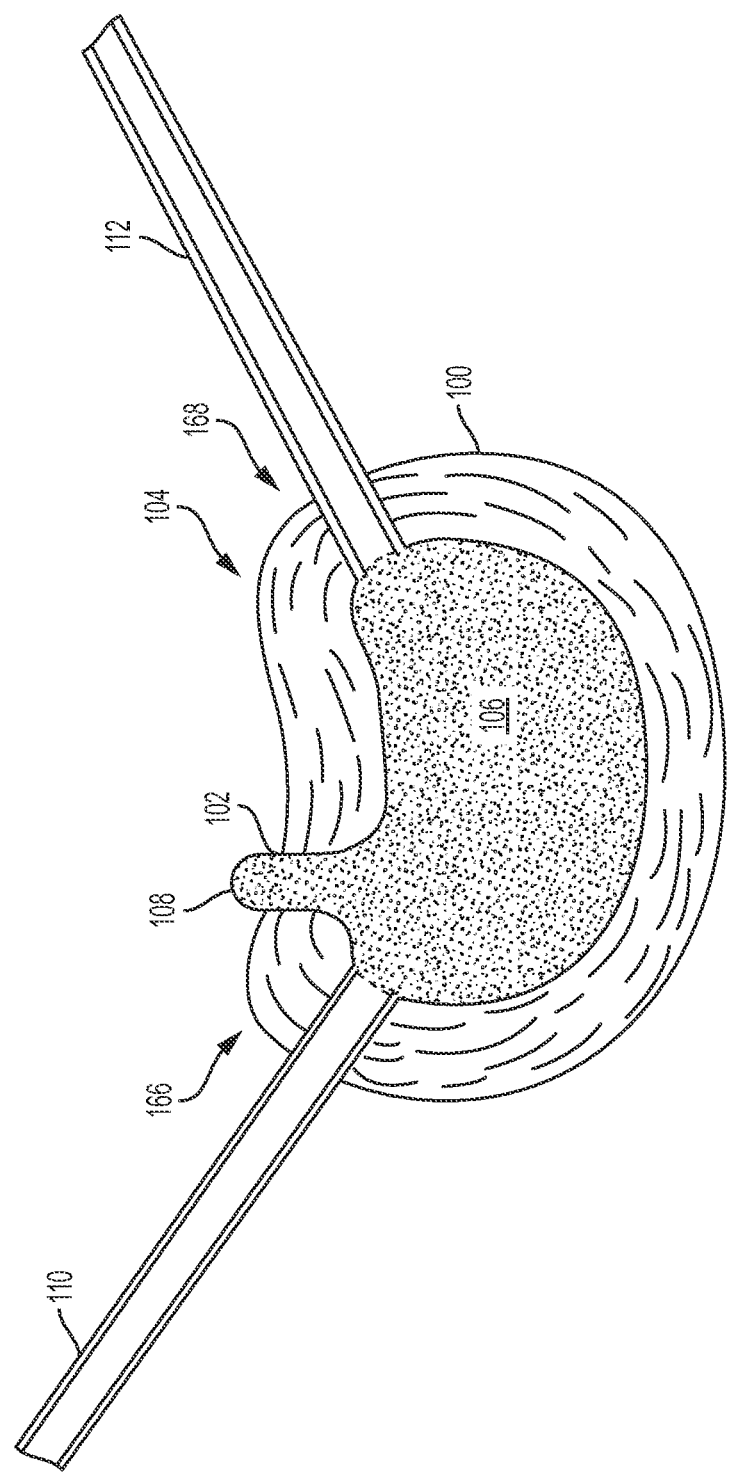
FIG. 1 is a sectional view of an annulus fibrosus with a defect and a disc herniation.

In the following detailed description, reference is made to the accompanying drawings, in which are shown exemplary but non-limiting and non-exhaustive embodiments of the invention. These embodiments are described in sufficient detail to enable those having skill in the art to practice the invention, and it is understood that other embodiments may be used, and other changes may be made, without departing from the spirit or scope of the invention. The following detailed description is, therefore, not to be taken in a limiting sense, and the scope of the invention is defined only by the appended claims. In the accompanying drawings, like reference numerals refer to like parts throughout the various figures unless otherwise specified.

Figure 2:
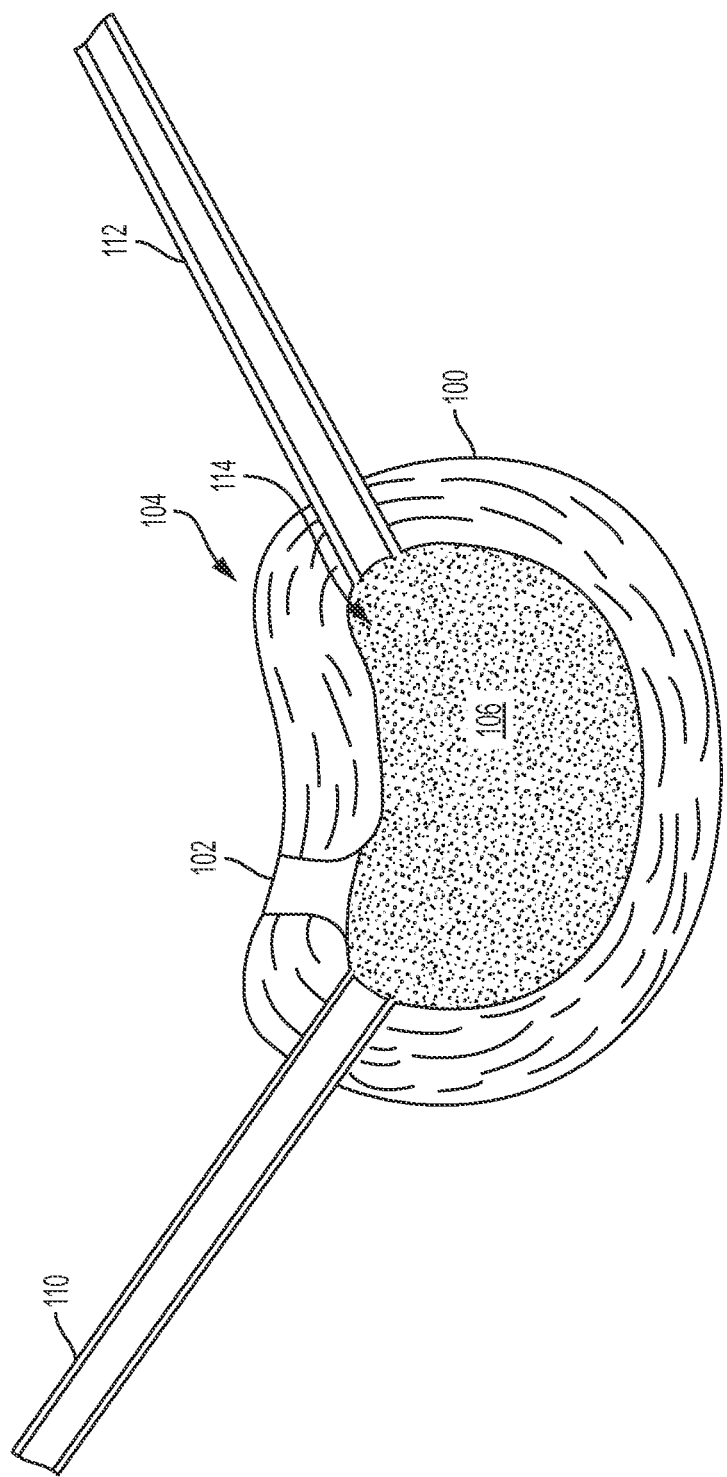
FIG. 2 is a sectional view of the annulus fibrosus of FIG. 1 with the disc herniation removed.
Figure 3:
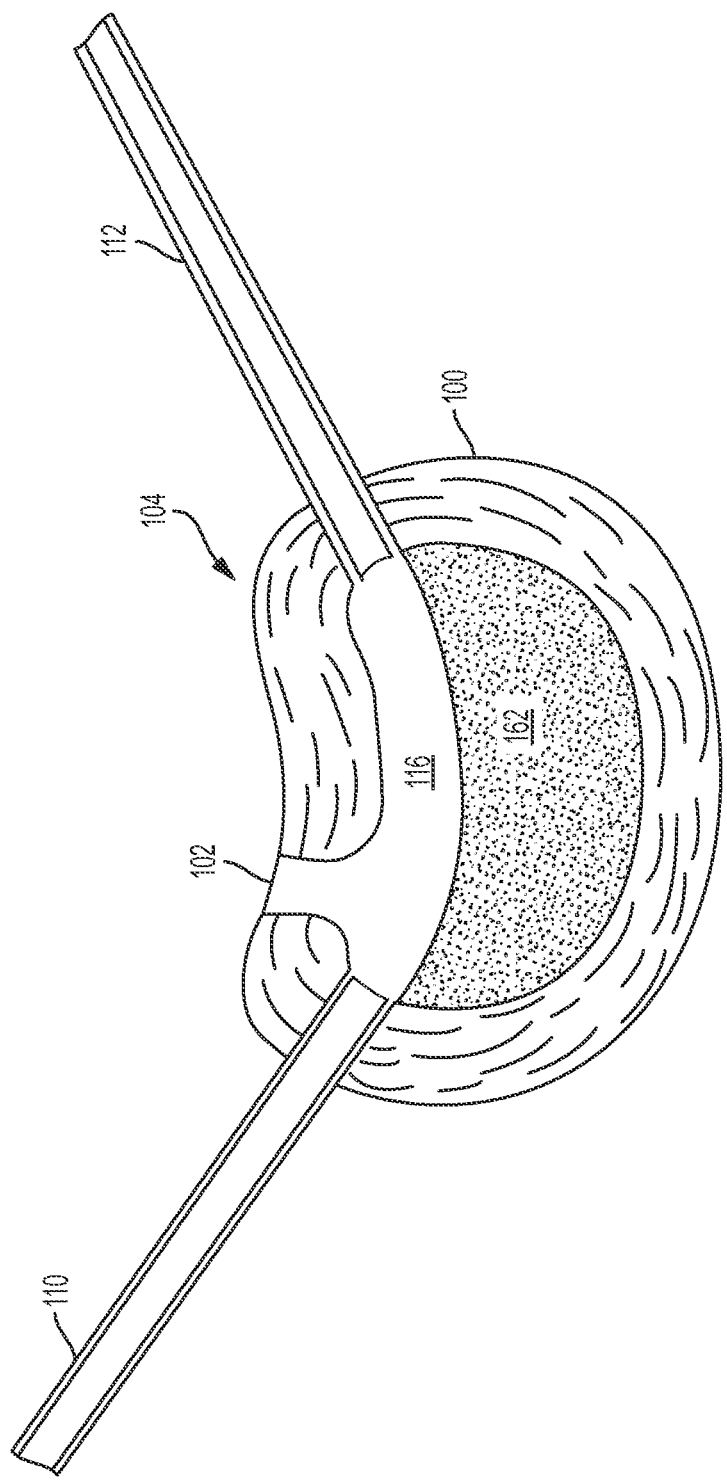
FIG. 3 is a sectional view of the annulus fibrosus of FIGS. 1 and 2 with a posterior portion of the disc removed to form a cavity for receiving an implant.

FIGS. 1-3 illustrate a process for preparing a spinal segment with a defect in the annulus for receiving an implant according to an embodiment of the present disclosure. Referring to FIG. 1, annulus fibrosus 100 has a defect 102 in the posterior portion 104 of annulus fibrosus 100. FIG. 1 illustrates a defect 102 with a herniated nucleus pulposus; that is nucleus pulposus 106 has extruded through the annular defect 102, forming a disc herniation 108. While a herniated nucleus pulposus has been illustrated here, it should be understood that defect 102 can be any defect such as a radial tear, a fissure, an opening or any other type of flaw in an annulus fibrosus, and includes those resulting from degenerative disc disease, trauma, or other conditions.

A first access cannula 110 and a second access cannula 112 are inserted through annulotomies in annulus fibrosus 100 to provide bilateral posterolateral percutaneous access to the disc cavity from a first posterolateral side of annulus 100 and a second posterolateral side of annulus 100. First and second access cannulas 110, 112 are preferably inserted through the safe zone defined by Kambin's triangle. First and second access cannulas 110, 112 are spaced away from annular defect 102 so that they are not immediately adjacent to defect 102. The access cannulas 110, 112 may be inserted by using sequentially dilating cannulas, by minimally invasive surgical approaches, or by other techniques known to those skilled in the art. The use of sequentially dilating cannulas to create annulotomies spreads the fibers of the annulus fibrosus without severing them. This allows the fibers to close when the cannulas are removed.

Referring to FIGS. 2 and 3, an initial step is to remove disc herniation 108 (if present). This may be accomplished using conventional surgical techniques known to those skilled in the art. Next, a partial nuclectomy is performed to remove the posterior portion 114 of nucleus pulposus 106, thereby leaving nucleus remnant 162. In some embodiments, the partial nuclectomy is performed using percutaneous techniques through first and second access cannulas 110, 112. This allows the controlled selective nuclectomy of the posterior nucleus, sparing the otherwise healthy nucleus pulposus 106 and nuclear remnant 162.

The partial nuclectomy creates a cavity 116 for receiving an implant 118. For clarity, cavity 116 is illustrated as a relatively large cavity in the accompanying figures; however, it should be understood that the cavity 116 is preferably a small cavity (for example, it may be approximately 1-2 mm wide). The posterior side of cavity 116 is formed by the inner wall of annulus fibrosus 100, while the anterior side of cavity 116 is formed by nucleus remnant 162. A physician may use a sizing balloon (i.e., a highly compliant balloon) with a contrast solution to measure the size and shape of cavity 116 while performing the nuclectomy to help ensure cavity 116 is properly formed, and to help determine the amount of curable material to be used in the implant.

Figure 4:
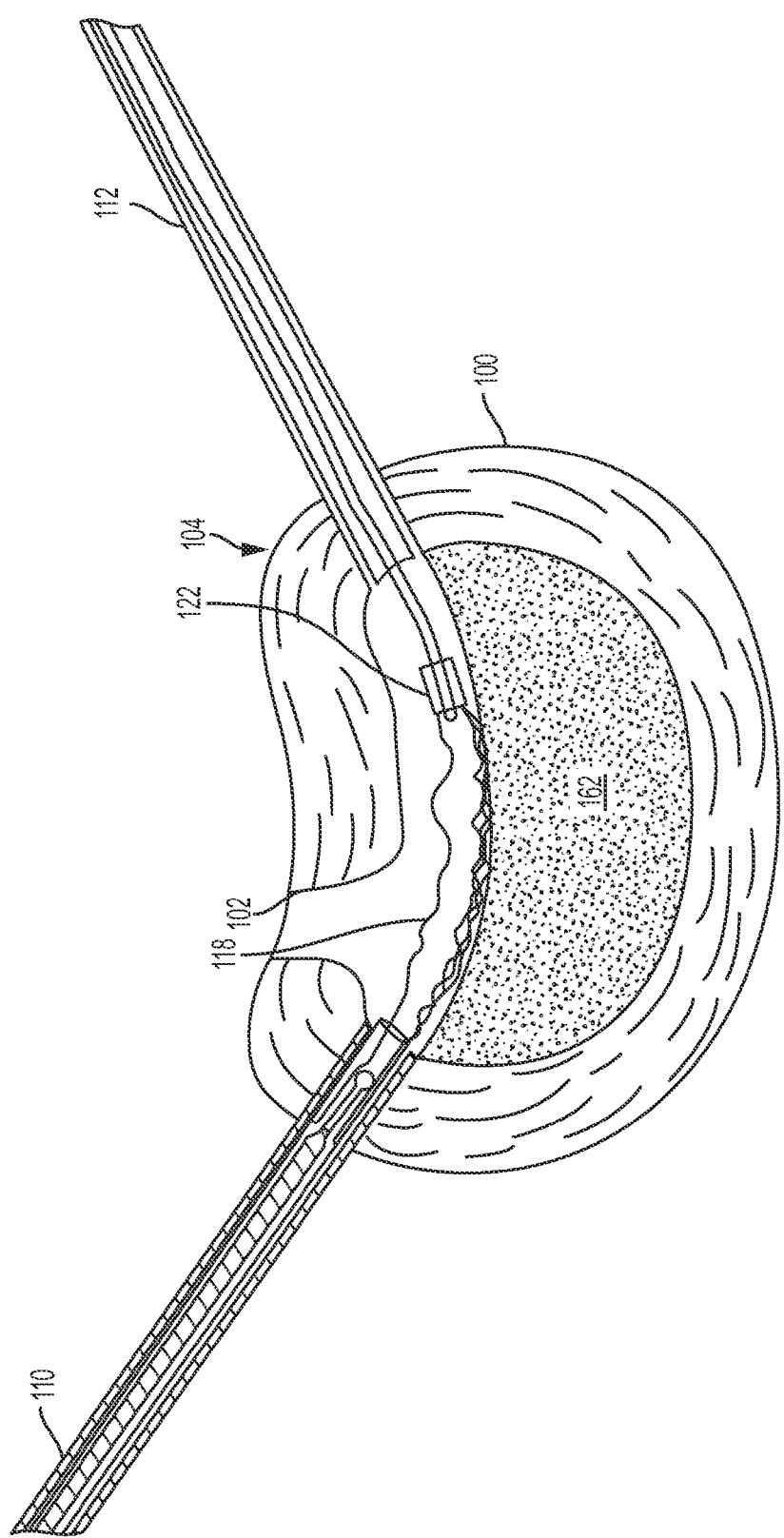
FIG. 4 is a sectional view of a step in delivering an implant into the disc space for receiving an implant.
Figure 5:
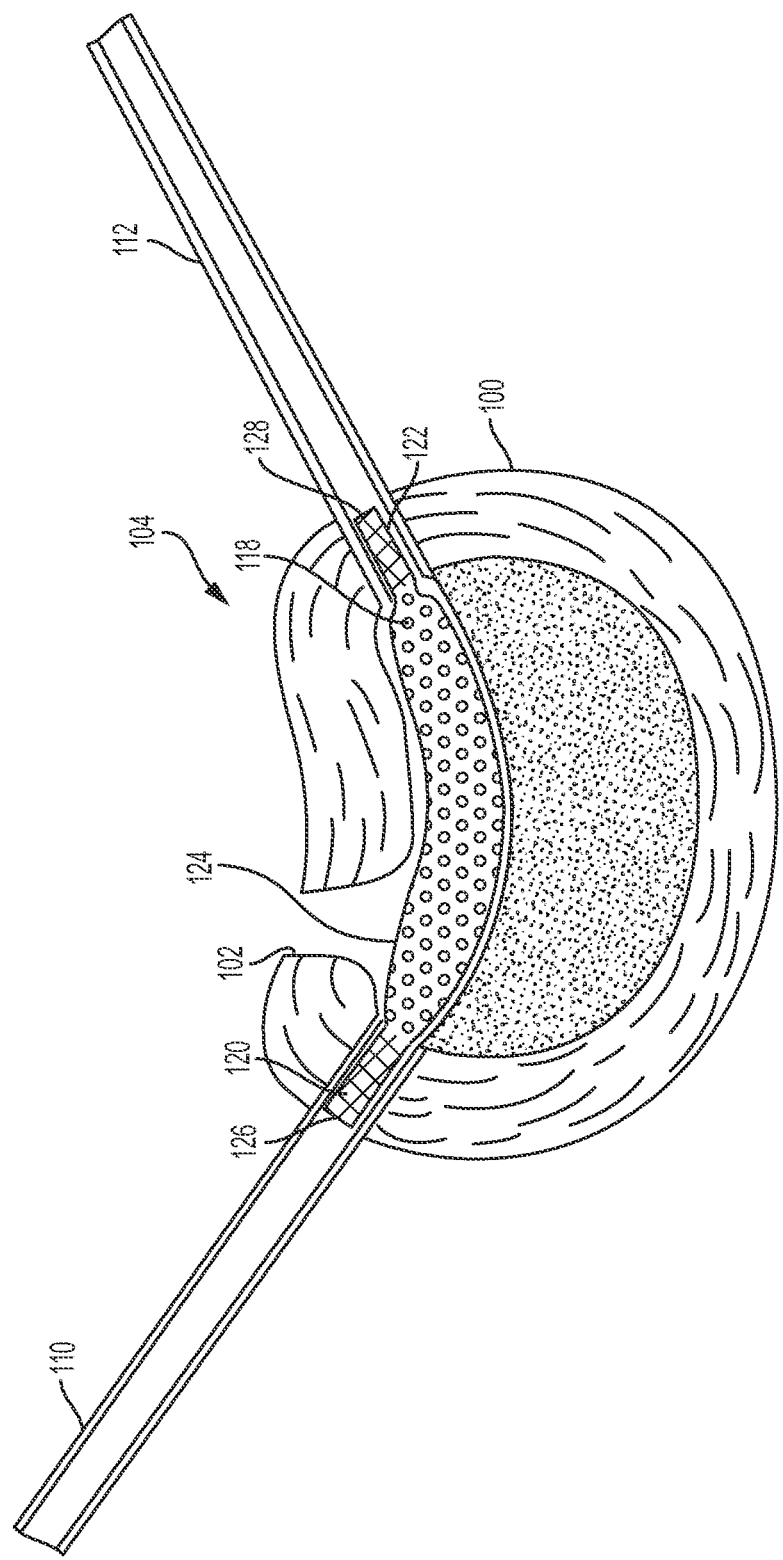
FIG. 5 is a sectional view of another step in delivering an implant into the disc space for receiving an implant.

Referring to FIGS. 4-5, an implant 118 is delivered to the disc cavity 116 through first and second access cannulas 110, 112. As shown in FIG. 4, deflated implant 118 is inserted through first access cannula 110 into disc cavity 118 so that second end 122 of implant 118 extends out of first access cannula 110 and into disc cavity 116. Second end 122 of implant 118 is then snared or otherwise captured using tools inserted through second access cannula 112 using techniques known to those skilled in the art, and implant 118 is the pulled through disc cavity 116 into the desired position. Second end 122 may have a loop of string or another retaining member to assist in snaring second end 122 and pulling it into the distal end of the second access cannula. One or more radiopaque markers may be provided on implant 118 to assist in placing implant 118 at a desired location.

Implant 118 comprises an elastomeric balloon 124 extending from first end 120 to second end 122. A first anchor 126 is coupled to first end 120 of balloon 124 and a second anchor 128 is coupled to second end 122 of balloon 124. First anchor 126 includes an inflation port 130 (see FIG. 7) for inflating balloon 124. First and second anchors 126, 128 may be formed integrally with balloon 124 or may be formed separately and then coupled to balloon 124.

Figure 7:
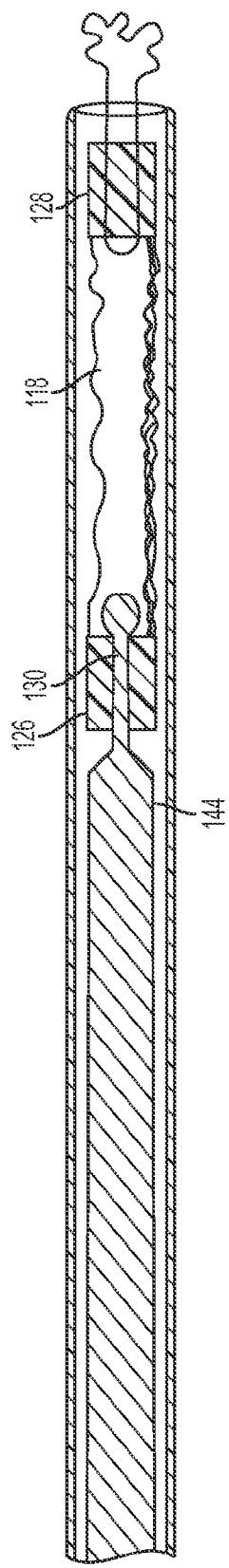
FIG. 7 is a sectional view of an implant loaded into a delivery cannula.

After implant 118 is placed in the desired position, an inflation stylus 144 which is inserted into inflation port 130 is used to deliver inflation material 132 to inflate balloon 124. Preferably, inflation stylus 144 is inserted into inflation port 130 before delivery through the catheter (i.e., it is pre-assembled, as shown in FIG. 7). In some embodiments, inflation material 132 is a curable silicone material. Inflated balloon 118 entirely fills cavity 116 so that it presses against the inner wall of annulus fibrosus 100, against the posterior side of nucleus remnant 162, and against the superior and inferior endplates. Preferably, the inflation takes place under observation (e.g., fluoroscopy), so that the balloon 124 may be inflated in an amount and pressure sufficient to substantially restore normal intradiscal pressure, normal disc height (i.e., the distance between adjacent vertebral endplates) and angulation, and normal biomechanical function. A second inflation port (not shown) may be utilized for inflating gas into a second balloon chamber (which is described in further detail below).

The implant 118 presses against and forms a substantially fluid tight seal with the inner wall of annulus fibrosus 100 to reinforce the posterior annulus fibrosus 100. If a defect 102 is present, implant 118 closes the defect 102. Preferably, implant 118 stretches across substantially all of the posterior portion of the annulus fibrous so that implant 188 reinforces the entire posterior of annulus fibrosus 100. This helps to reduce the risk of recurrent disc herniation. Sealing the nuclear space helps preserve intradiscal pressure and minimize seepage of nucleus pulposus breakdown products through the annular tear or defect, which can cause patient discomfort.

Figure 6:
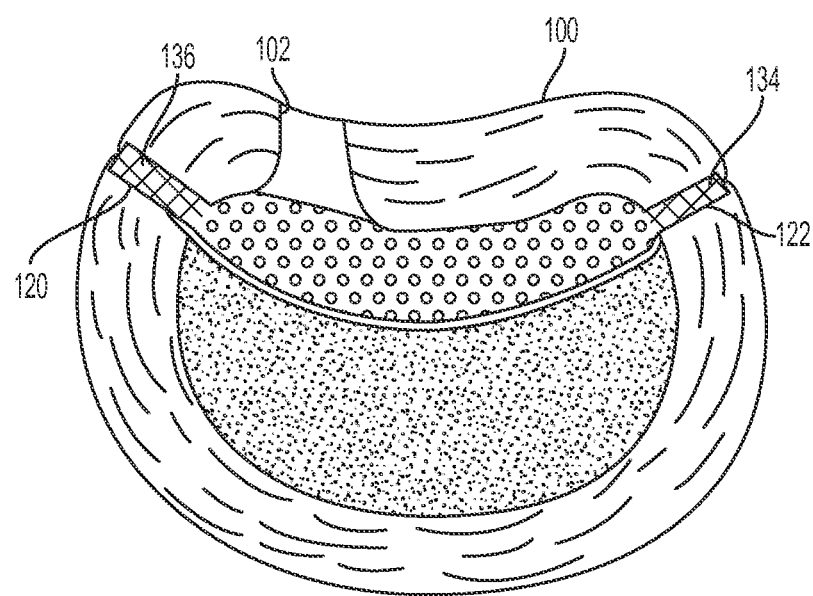
FIG. 6 is a sectional view of an implant after insertion.

After inflation material 132 is cured, first and second access cannulas 110, 112 are removed, and as shown in FIG. 6, first and second anchors 126, 128, are anchored to first and second openings (or annulotomies) 134, 136 formed by the first and second access cannulas 110, 112. When annulotomies 134, 136 are formed by spreading the fibers of annulus fibrosus 100, the fibers tighten and contract when cannulas 110, 112 are removed due to the elasticity of the fibers of annulus fibrosus 100, and thereby engage first and second ends 120, 122 of balloon 124. The widening of the disc space (i.e., the restoration of normal disc height) contributes to the tightening of the fibers of annulus fibrosus 100. This fixates ends 120, 122 to annulus fibrosus 100 on opposite sides of defect 102 at annulotomies 134, 136 which are spaced away from defect 102 towards the lateral sides of annulus 100. Furthermore, in the case of a herniated nucleus pulposus, anchors 126, 128 are spaced away from the surgical site used to remove disc herniation 108. Anchors 126, and 128 help reduce the risk of implant 118 from being expelled from disc cavity 116 or migrating within disc cavity 116.

Figure 8:
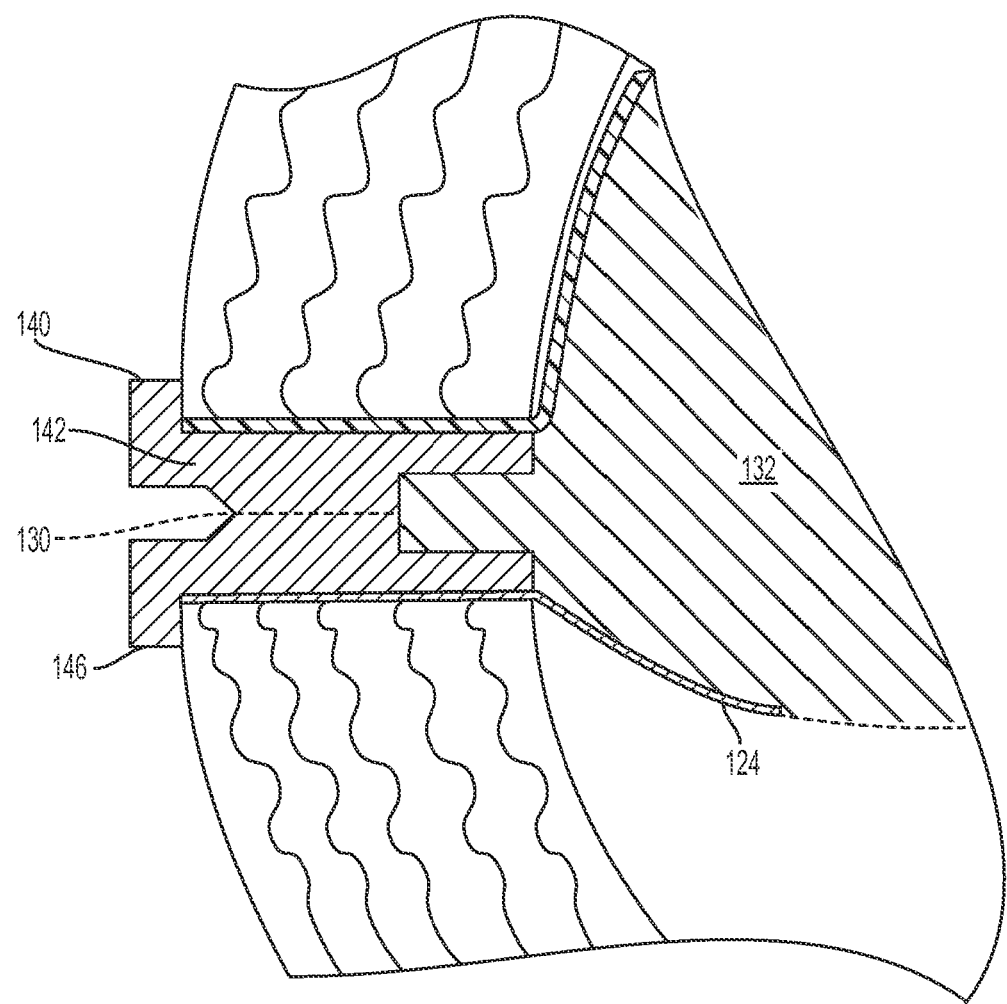
FIG. 8 is a sectional view of an anchoring mechanism for anchoring the implant of FIG. 4.
Figure 9:
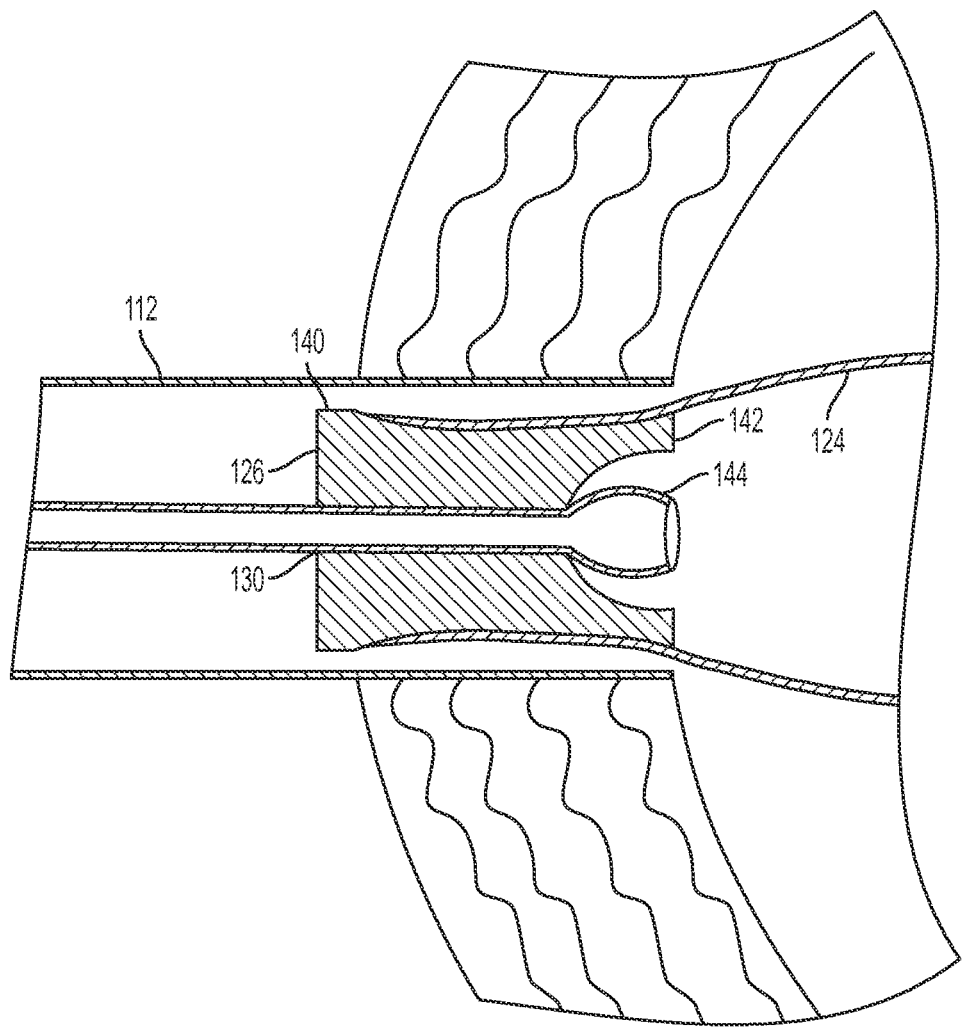
FIG. 9 is a sectional view of the anchoring mechanism of FIG. 8, in a compressed position in the delivery cannula.
Figure 10:
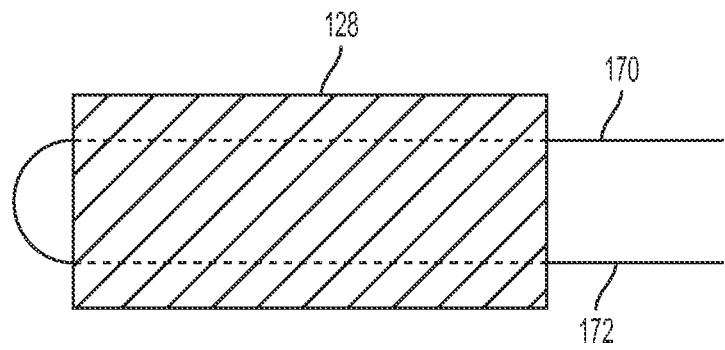
FIG. 10 is a sectional view of another anchoring mechanism.
Figure 11:
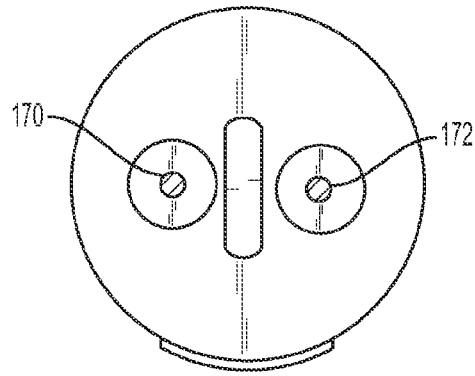
FIG. 11 is a plan view of a retaining member.
Figure 12:
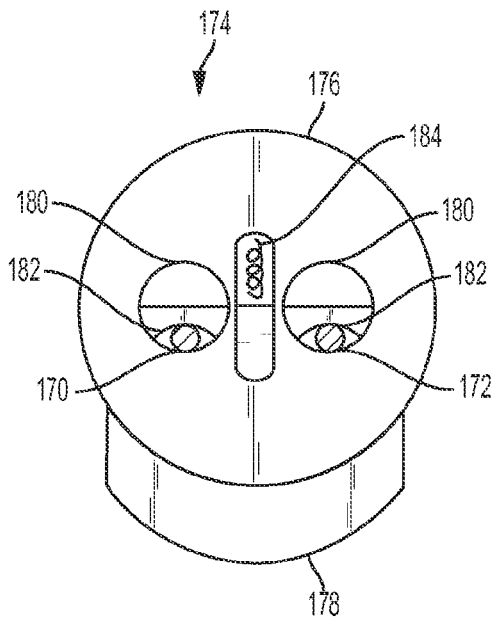
FIG. 12 is a plan view of the retaining member of FIG. 11, in an open position.

Referring to FIGS. 8-10, first anchor 126 and second anchor 128 may have additional features to minimize the possibility of the anchors being pulled through annulus fibrosus 100. First anchor 126 may comprise a cylindrical stem portion 142 with a flange 140. During insertion, cylindrical stem portion 142 is stretched over inflation stylus 144 to open inflation port 130 to allow curable material to flow into balloon 124. When inflation stylus 144 is retracted, cylindrical stem portion 142 collapses to act as a valve to close inflation port 130 to seal balloon 124 and prevent inflation material 132 from escaping balloon 124. The inflation stylus and stem portion 142 may have features to prevent inadvertent disconnection or leakage (such as an enlarged discharge end or corresponding groove and slot features). Flange 140 is compressed by the delivery cannula and access cannula 110 during delivery. Upon removal of inflation stylus 144 and access cannula 110, flange 140 expands to form an expanded portion 146 which help prevent cylindrical stem portion 142 from being pulled through annulus fibrosus 100.

Figure 13:
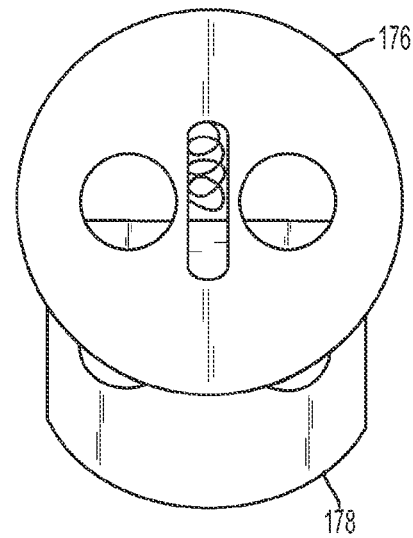
FIG. 13 is a plan view of the retaining clip of FIG. 11, in a closed position.
Figure 14:
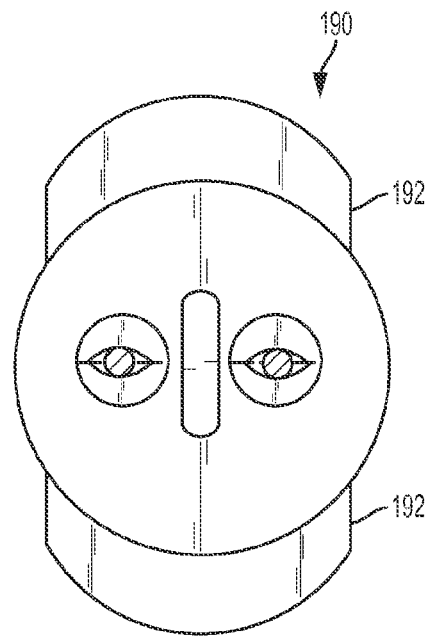
FIG. 14 is a plan view of an alternative embodiment of a retaining member.
Figure 15:
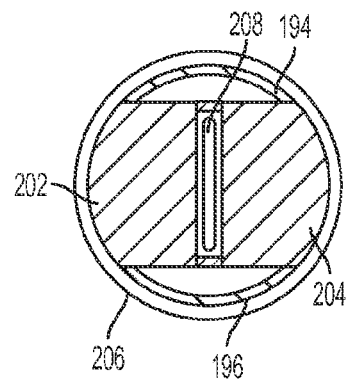
FIG. 15 is a sectional view of a retaining member in accordance with another embodiment, in an open position.
Figure 17:
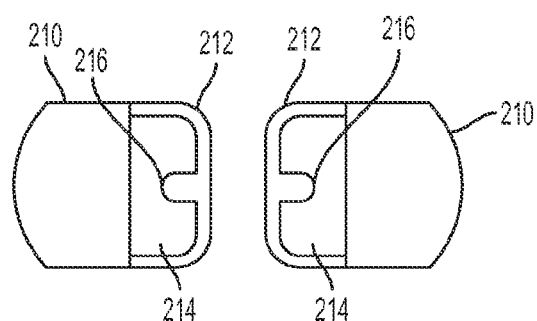
FIG. 17 is a sectional view of two retaining members for use in the retaining member of FIG. 15.

Referring to FIGS. 10-14, second anchor 128 is coupled to second end 122 of balloon 124. Second anchor 128 may be a cylinder or any other suitable shape. Second anchor 128 is delivered through the disc space 116 and into the distal end of the second cannula. Second anchor 128 may have a flange or expanded portion such as first anchor 126. Alternatively, second anchor 128 may use a different anchoring mechanism. In one embodiment, second anchor 128 comprises a loop of material with first and second sides 170, 172 which can be formed of a surgical suture material. A physician may snare the loop and use the loop to pull the second anchor into the second cannula during the implantation procedure. A retaining member (or clip) 174 can be attached to the strings and drawn tight against annulus fibrosus 100 to help hold second anchor 128 in place. In some embodiments, retaining member 174 comprises a first member 176 with a sliding plate 178 slidably connected to it. First member 176 has at least one and preferably two apertures 180. Sliding plate 178 has at least one and preferably two apertures 182. A biasing member 184 biases sliding plate 178 outwardly (as shown in FIG. 13). When sliding plate 178 is squeezed close, apertures 180 and 182 are aligned, and first and second sides 170, 172 of the loop of surgical suture material can be placed through the apertures. A user must cut the loop into two separate strings 170, 172 so that they can be placed through the apertures. When released, plate 178 is biased outward so that strings 170, 172 are trapped by apertures 180, 182 (see FIG. 12). A user may slide retaining member 174 down strings 170, 172 until it is tight against the outer margin of annulus fibrosus 100. In some embodiments, the outer diameter of retaining member 174 in the open position is substantially the same size as the inner diameter of second access cannula 112 so that sliding plate 178 is held into the open position until it exits the distal end of second access cannula 112. Although two strings are shown in the illustrated embodiment, any number of strings may be used, from one or more. Similarly, retaining members with a different number of sliding plates may be used, as shown in FIG. 14, which illustrates a retaining member 190 with two sliding plates 192.

FIGS. 15-20 illustrate another embodiment of a retaining member and an anchoring mechanism. Retaining member 194 comprises an outer retaining ring 196 with first and second opening 198, 200 for receiving first and second sliding members 202, 204, respectively. First and second sliding members 202, and 204 slide in and out (i.e., toward and away from the center of retaining ring 198), and are biased outward by biasing members such as springs (which are not illustrated for clarity). The outer diameter of retaining ring 196 is substantially the same as the inner diameter of a delivery cannula 206. First and second sliding members 202, 204 are held in the open position (i.e., squeezed together so that slot 208 is open) by the delivery cannula 206. Sliding members 202, 204 are preferably the same shape and configuration. Each sliding member comprises a flat member 210 with a protruding u-shaped member 212 which forms an aperture 214. A tongue 216 extends from u-shaped member 212. The u-shaped member 212 is offset from the centerline of the flat member 210 so that the sliding members have be inserted into retaining ring 196 in different orientations. This way, u-shaped members 212 form complementary sliding members (referring to FIG. 18) and do not interfere with one another when placed in the open position. Retaining member 194 may be formed of any biocompatible material, such as stainless steel or polymeric material.

Figure 16:
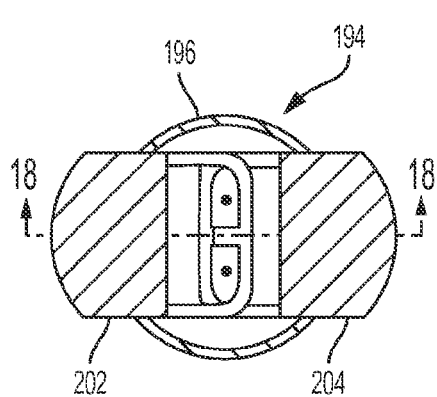
FIG. 16 is a sectional view of the retaining member of FIG. 15, in an open position.
Figure 18:
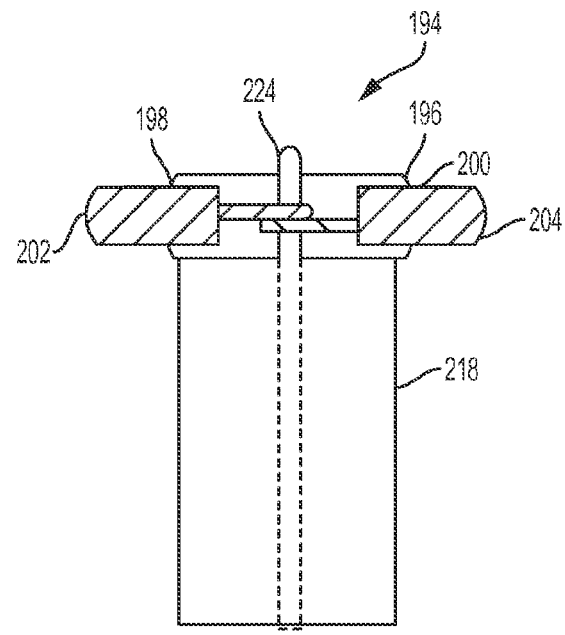
FIG. 18 is a sectional view of the retaining member of FIG. 15 taken along line 18-18.

To use retaining member 194, the sliding plates are squeezed together so that apertures 214 of the two plates are aligned and form slot 208. String 170, 172 are placed through slot 208, and slot 208 is loaded into cannula 206. Retaining member 194 is then delivered down delivery cannula 206 by a pusher (not illustrated) until it is adjacent the second anchor 216. The pusher can be a cannula with an outer diameter which fits snugly within delivery cannula 206. While holding retaining member 194 firmly against second anchor 218, the delivery cannula is removed, allowing the biasing members to close sliding members 202, 204 (i.e., press the sliding members outward to close slot 208, as shown in FIGS. 16 and 18). In some embodiments, retaining ring 196 and sliding plates 202, 204 may have locking features to lock the sliding plates in the closed position once the retaining member 194 is in place. Once sliding plates 202, 204 expand outward from retaining ring 196, they form an enlarged portion which helps anchor the end of the implant and prevent the anchor from being pulled through the annulus fibrosus.

Figure 19:
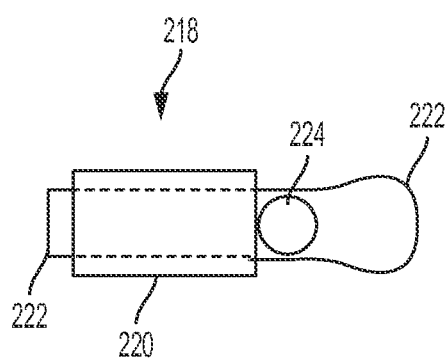
FIG. 19 is a top view of another embodiment of an anchoring mechanism.
Figure 20:
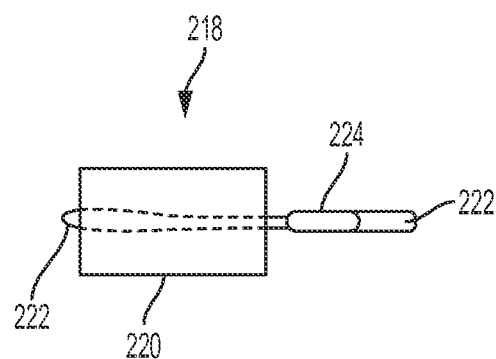
FIG. 20 is a side view of the anchoring mechanism of FIG. 19.
Figure 22:
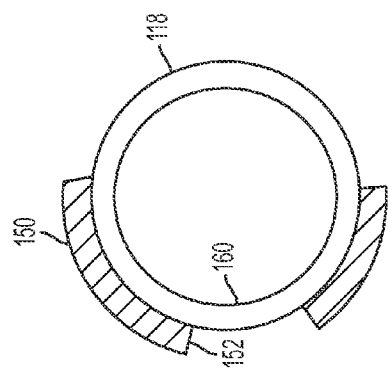
FIG. 22 is another sectional view of the implant of FIG. 21 taken along line 21-21, before inflation.
Figure 24:
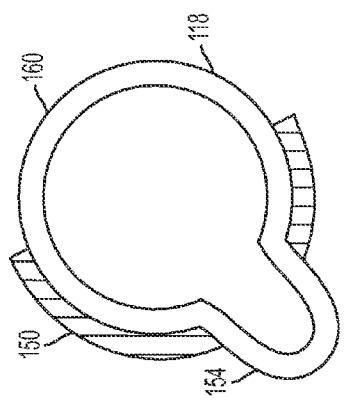
FIG. 24 is another sectional of the implant of FIG. 21 taken along line 24-24, after inflation.
Figure 21:
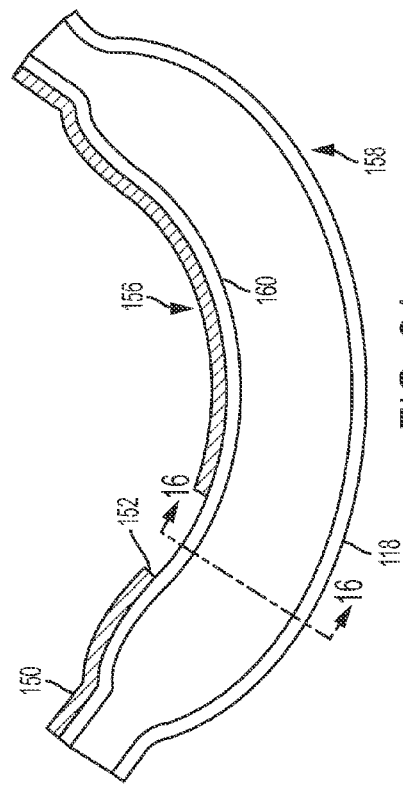
FIG. 21 is a sectional view of another embodiment of an implant for repairing an annulus fibrosus, before inflation.
Figure 23:
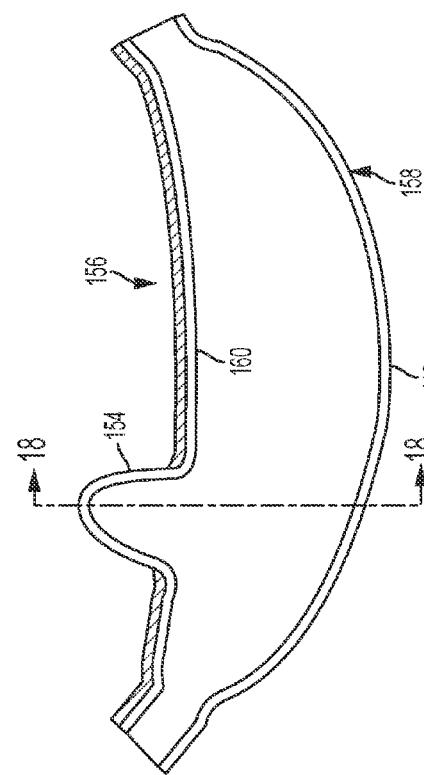
FIG. 23 is a sectional of the implant of FIG. 21, after inflation.
Figure 25:
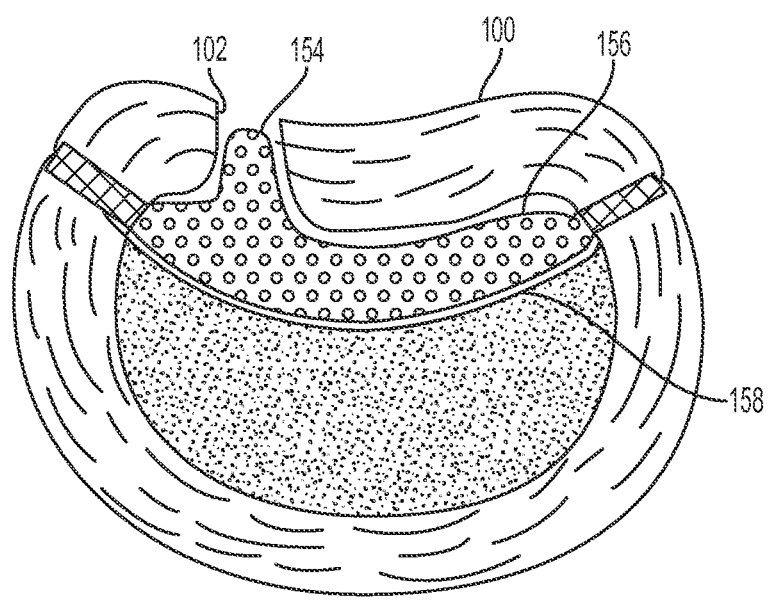
FIG. 25 is a sectional view of the implant of FIG. 21, after implantation and inflation.

FIGS. 19 and 20 illustrate an anchor 218 which is particularly suitable for use with the retaining member of FIGS. 15-18. Anchor 218 comprises a cylindrical member 220 with an embedded loop of wire or string 222. Loop 222 is preferably formed of a material which retains its shape, such as wire or stiff nylon. Loop 222 can be used to snare anchor 218 and pull it into the proper position within the distal segment of the second cannula, as described previously. Preferably, loop 222 is long enough that it can be pulled out the end of second delivery cannula 212, although it is shown shorter in the illustrations for clarity. A second anchoring loop 224 is placed near the anchor and fastened to loop 222. When anchor 218 is used with retaining member 194, the tongues 216 extend into anchoring loop 224 when tongues 216 are closed to form a positive connection. Thus, instead of relying solely on friction between loop 222 and sliding plates 202, 204, anchoring loop 224 is positively locked to retaining member 194.

Referring to FIGS. 21-25, in some embodiments balloon 124 of implant 118 may comprise a multi-layered balloon. For example, balloon 124 may have a reinforcement layer 150 on the posterior portion 156 of the implant 118 to strengthen the implant and aid incorporation of the implant 118 into the annulus fibrosus. Reinforcement layer 150 may be located on the interior or exterior of balloon 124. Reinforcement layer 150 may be any biocompatible material with a high strength, such as a woven, knitted or braided textile or an ePTFE material. Other fiber deposition techniques such as electrospinning may be used to form reinforcement layer 150. After balloon 124 is inflated and the curable material is cured, the implant 118 comprises a flexible and resilient structure which is resistant to migration through annular defect 102.

In some embodiments, balloon 124 comprises a silicone material. In some embodiments, balloon 124 comprises a PTFE material (such as an expanded PTFE material). A layer of carbon material may be included to enhance the bond between the PTFE material and the curable material. The porosity of the PTFE material may be controlled to allow partial penetration of the curable material while it is in the liquid state to create an integrated structure after curing which minimizes the possibility of delamination. Balloon 124 may be porous to allow the escape of air in the system or air trapped in the liquid silicone during mixing.

In some embodiments, balloon 124 may have differential and directional expandability to control the direction and amount of expansion of balloon 124. In some embodiments, balloon 124 has segments of increased base and dimensional stability. In some embodiments, the surface of balloon 124 may have a unique surface topography to enhance desired characteristics. For example, the surface may have increased lubricity to reduce friction against vertebral endplate surfaces and enhance tissue in-growth in the annulus fibrosus. Balloon 124 may be formed in various shapes to fit different cavity configurations.

In some embodiments, balloon 124 is adapted to fill an annular defect. Outer layer 150 of balloon 124 may have at least one opening 152 through which inner layer 160 protrudes when the implant 118 is inflated within cavity 116. By aligning opening 152 in outer layer 150 with defect 102 in annular fibrosis 100, inner layer 160 protrudes out opening 152 to form a protrusion 154. Protrusion 154 acts as a plug to fill the annular defect 102 and the associated cavity, which assists in treating annular defect 102. In some embodiments, inner layer 160 of balloon 124 comprises a compliant material, such as a silicone membrane; and outer layer 150 comprises a material which is less compliant than inner layer 160. In some embodiments, outer layer 150 is fiber reinforced. The opening 152 in less compliant outer layer 150 allows compliant inner layer 160 to expand therethrough.

In some embodiments, anterior wall 158 of balloon 124 is relatively thinner or more compliant than posterior wall 156 of balloon 124. As balloon 124 expands, differential expansion occurs with more compliant anterior wall 158 expanding more than that of posterior wall 156. In some embodiments, less compliant posterior wall 156 comprises one or more layers of a matrix of spun fibers. Multi-layered designs may be configured to strengthen or otherwise affect certain properties of the balloon, including mechanical properties such as burst strength and puncture resistance.

Use of multilayered and differential balloon walls may facilitate various aspects of manufacturing, deployment and therapies involving nuclear implants. For example, as discussed above, a multi-layered design may be thinner and/or more compliant along its anterior wall 156. This may enable implant balloon 124 to be folded or otherwise packed into a smaller delivery configuration. Additionally, smaller profiles may require access cannulas having a smaller diameter and smaller annulotomy puncture, which decreases the possibility of implant extrusion.

Posterior wall 156 of a multilayer nuclear implant balloon 124 may be formed of multiple layers of the same material, or multiple layers of different materials. In some embodiments, layers may be formed of materials with similar compliance, providing an additive effect. In other embodiments, layers may be formed of different materials and formed independently, allowing for properties of each layer to be individually optimized.

Balloon 124 may be designed to expand symmetrically or asymmetrically. The balloon wall may comprise at least one radially asymmetrically dilatable portion, wherein the cross-section has one or more regions that differ in terms of compliance, strength and other characteristics. Such balloons provide enhanced performance though use of differential and directional expandability of the implant increased dimensional stability, improved cavity contour and improved tissue incorporation.

In some embodiments, balloon 124 has areas of electrospun polymeric material in combination with a silicone material, and other areas of uncovered silicone material. The electrospun polymeric material may comprise expanded PTFE (ePTFE). Application of PTFE to posterior wall 156 of implant 118 at least partially constrains inflation along the inner annulus and provides enhanced performance through use of differential and direction expandability. Furthermore, PTFE enhances soft tissue purchase by encouraging fibrocyte migration and incorporation of the implant with the posterior annulus. This helps guard against further disc herniation.

Balloon 124 may comprise flexible materials which accommodate a low-profile delivery without compromising strength and elasticity. In some embodiments, balloon 124 comprises an ultra-high molecular weight polyethylene (UHMwPE) material, such as DYNEEMA®, available from Royal DSM of Herleen, Netherlands. In some embodiments, balloon 124 may be coated with a hydrophilic material to increase lubricity.

In some embodiments, anterior wall 158 is relativity thinner and more compliant than posterior wall 156 so that it expands more than posterior wall 156, sequestering the remaining portion of nucleus pulposus 106 and providing disc space widening and angle restoration.

In one embodiment the posterior portion of the nuclear implant consists of a flexible tubular three-dimensionally braided structure of metal or polymeric monofilaments, and polymeric multifilament yarns. The metallic thread elements or strands are favored for applications requiring additional reinforcement and effective protection against migration of the implant through a large annulus defect or a very weakened posterior annulus.

Figure 26:
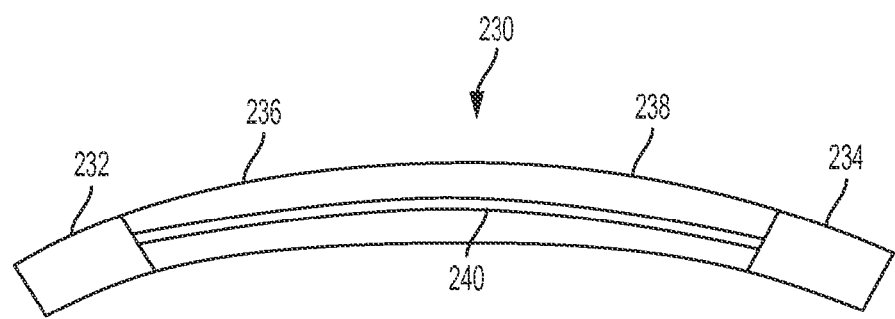
FIG. 26 is a sectional view of another embodiment of an implant for repairing an annulus fibrosus, before inflation.
Figure 27:
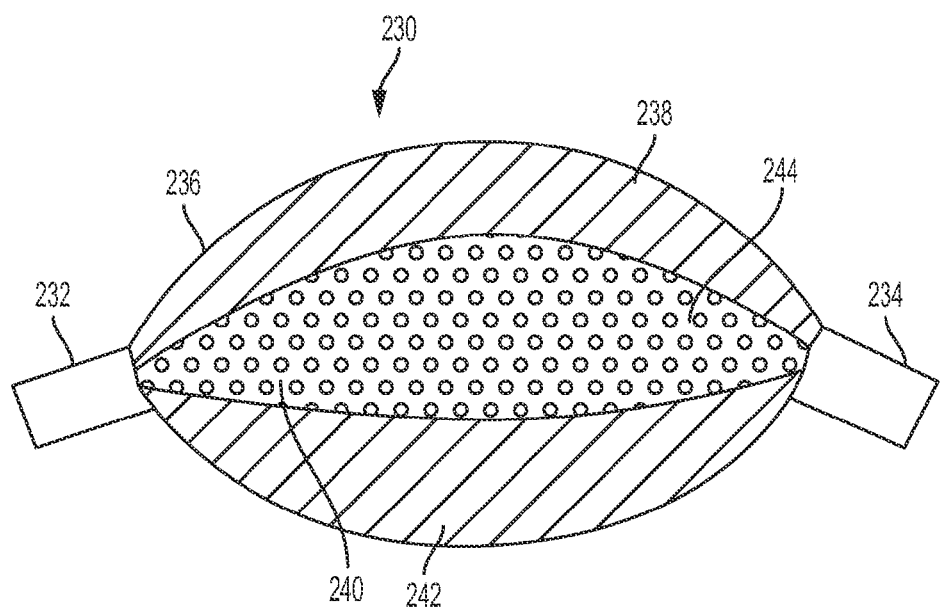
FIG. 27 is a sectional view of the implant of FIG. 23, after inflation.
Figure 28:
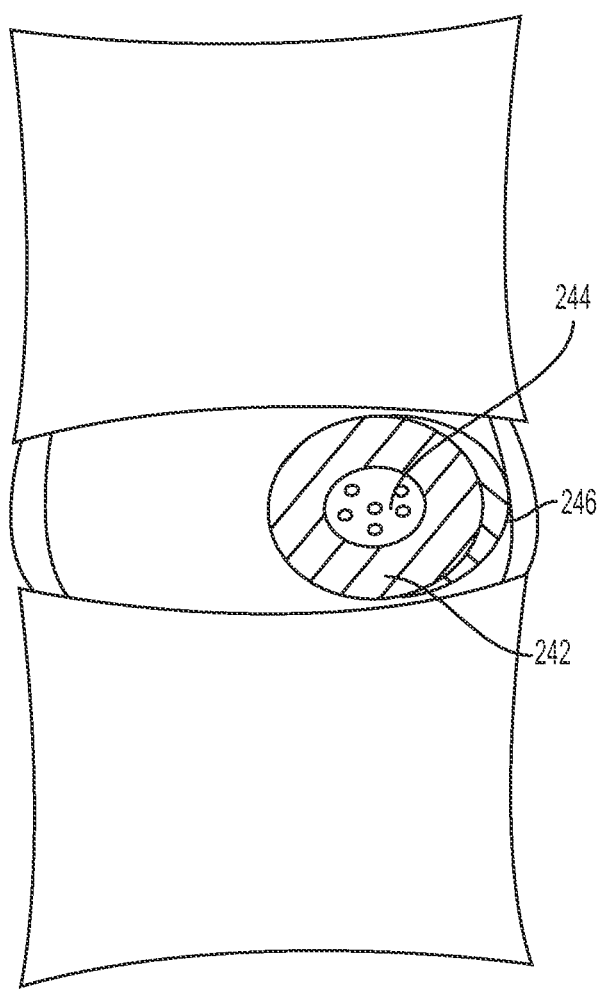
FIG. 28 is a sectional view of the implant of FIG. 23, after implantation and inflation.

Referring to FIGS. 26-28, in some embodiments, an implant 230 for a partial nuclectomy comprises a proximal anchor 232, a distal anchor 234, and an inflatable balloon 236 extending therebetween. The inflatable balloon 236 is a multi-chambered balloon, having at least a first chamber 238 and a second chamber 240. In one embodiment, second chamber 240 is disposed inside first chamber 238 and is completely surrounded by first chamber 238. The inner and outer chamber may be filled with different materials to provide implant 230 with desired characteristics. It should be understood to one of ordinary skill in the art that any device, apparatus and/or system suitable for injecting fluid can be used to inflate first and second chambers 238, 240. In some embodiments, first chamber 238 is filled with a curable elastomeric material 242, while second chamber 240 is filled with a compressible material 244 (i.e., a gaseous material). This allows the implant 230 to absorb sudden increases in intra-discal pressure, acting effectively as a shock absorber. Like the other embodiments, the balloon 236 can comprise multiple layers, and a reinforcing layer 246 can be provided.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

What is claimed is:

1. An apparatus for reinforcing a damaged annulus fibrosus, comprising:
   an inflatable balloon having a first end, a second end, a posterior portion which is adapted to seal against an annulus fibrosus, and an anterior portion which is more compliant than the posterior portion;
   a first anchor coupled to the first end of the inflatable balloon, the first anchor being adapted to anchor the first end of the inflatable balloon to a first location of the annulus fibrosus at a first lateral side of the annulus fibrosus; and
   a second anchor coupled to the second end of the inflatable balloon, the second anchor being adapted to anchor the second end of the inflatable balloon to a second lateral side of the annulus fibrosus.

2. The apparatus of claim 1, further comprising a reinforcing layer coupled to the posterior portion of the balloon.

3. The apparatus of claim 1, wherein
   the posterior portion of the balloon further comprises a reinforcing layer coupled to a posterior side of the balloon so that the posterior portion is substantially non-compliant; and
   the anterior portion of the balloon comprises a silicone material so that the anterior portion is substantially compliant.

4. The apparatus of claim 1, wherein the inflatable balloon comprises silicone.

5. The apparatus of claim 1, wherein the inflatable balloon comprises PTFE.

6. The apparatus of claim 5, further comprising a carbon layer disposed on an inner surface of the inflatable balloon.

7. The apparatus of claim 5, wherein the PTFE balloon is porous.

8. The apparatus of claim 1, wherein the first anchor further comprises at least one inflation port for injecting an inflation material into the inflatable balloon.

9. The apparatus of claim 8, wherein the second anchor further comprises at least one inflation port for injecting an inflation material into the inflatable balloon.

10. The apparatus of claim 1, further comprising a curable material in the inflatable balloon.

11. The apparatus of claim 1, wherein the posterior portion comprises multiple layers.

12. The apparatus of claim 11, wherein an outer layer in the posterior portion comprises an opening for allowing an inner layer of the posterior portion to protrude therethrough upon inflation.

13. The apparatus of claim 1, wherein the inflatable balloon comprises an electrospun polymeric material.

14. The apparatus of claim 1, wherein the first anchor comprises an expanded portion for helping to prevent the first anchor from being pulled through the annulus fibrosus.

15. The apparatus of claim 1, wherein the second anchor comprises a retaining member with an expanded portion for helping to prevent the second anchor from being pulled through the annulus fibrosus.

16. The apparatus of claim 1, wherein the inflatable balloon comprises multiple layers adapted to provide different properties to the inflatable balloon.

17. The apparatus of claim 1, wherein the second anchor comprises first and second loops of material extending from the second anchor.

18. The apparatus of claim 17, further comprising a retaining member for engaging one of the first and second loops of material.

* * * * *